United States Patent
DiCaprio

(12) 
(10) Patent No.: US 6,656,211 B1
(45) Date of Patent: Dec. 2, 2003

(54) STENT DELIVERY SYSTEM WITH IMPROVED TRACKING

(75) Inventor: Fernando DiCaprio, Mendota Heights, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 122 days.

(21) Appl. No.: 09/697,608

(22) Filed: Oct. 26, 2000

(51) Int. Cl.[7] ................................................. A61F 2/06
(52) U.S. Cl. ...................... 623/1.11; 606/108; 606/194; 604/96.01
(58) Field of Search ................ 604/103.03, 103.08, 604/103.09, 103.1, 529, 527, 533, 96.01, 915; 606/193, 108, 192, 194; 623/1.11, 1.12, 1.23

(56) References Cited

U.S. PATENT DOCUMENTS

| | | | |
|---|---|---|---|
| 5,026,377 A | * 6/1991 | Burton et al. | 606/108 |
| 5,242,396 A | * 9/1993 | Evard | 604/103.09 |
| 5,653,691 A | 8/1997 | Rupp et al. | 604/96 |
| 5,702,364 A | 12/1997 | Euteneuer et al. | 604/96 |
| 5,810,871 A | * 9/1998 | Tuckey et al. | 606/108 |
| 5,944,726 A | 8/1999 | Blaeser et al. | 606/108 |
| 5,968,069 A | 10/1999 | Dusbabek et al. | 606/194 |
| 5,980,530 A | * 11/1999 | Willard et al. | 606/195 |
| 5,980,533 A | 11/1999 | Holman | 606/108 |
| 6,007,543 A | 12/1999 | Ellis et al. | 606/108 |
| 6,033,433 A | 3/2000 | Ehr et al. | 623/1 |
| 6,096,056 A | 8/2000 | Brown | 606/194 |
| 6,120,533 A | * 9/2000 | Fischell | 606/108 |
| 6,123,712 A | * 9/2000 | Di Caprio et al. | 606/108 |
| 6,174,316 B1 | * 1/2001 | Tuckey et al. | 606/108 |
| 6,174,329 B1 | * 1/2001 | Callol et al. | 606/194 |
| 6,221,043 B1 | * 4/2001 | Fischell et al. | 604/103.06 |
| 6,221,097 B1 | * 4/2001 | Wang et al. | 606/108 |
| 6,280,412 B1 | * 8/2001 | Pederson et al. | 604/103.07 |
| 6,371,962 B1 | * 4/2002 | Ellis et al. | 606/108 |

OTHER PUBLICATIONS

U.S. patent application Ser. No. 08/511,076, Brown et al., filed Aug. 3, 1995.
U.S. patent application Ser. No. 09/087,526, Vrba, filed May 29, 1998.
U.S. patent application Ser. No. 09/283,375, Mareiro et al., filed Mar. 31, 1999.
U.S. patent application Ser. No. 09/407,836, Wang et al., filed Sep. 28, 1999.
U.S. patent application Ser. No. 09/427,805, Wang et al., filed Oct. 27, 1999.

* cited by examiner

*Primary Examiner*—Corrine McDermott
*Assistant Examiner*—William H Matthews
(74) *Attorney, Agent, or Firm*—Vidas, Arrett & Steinkraus PA

(57) ABSTRACT

A medical device delivery system comprises an inner tube and at least one securement hub disposed about the distal end of the inner tube. The securement hub comprises an inner layer of material and an outer layer of material. The inner layer of material is more rigid than the outer layer of material. A balloon, in fluid communication with an inflation lumen, may be disposed about the securement hub and the distal end of the inner tube. The medical device delivery system may be used to deliver medical devices such as stents.

24 Claims, 3 Drawing Sheets

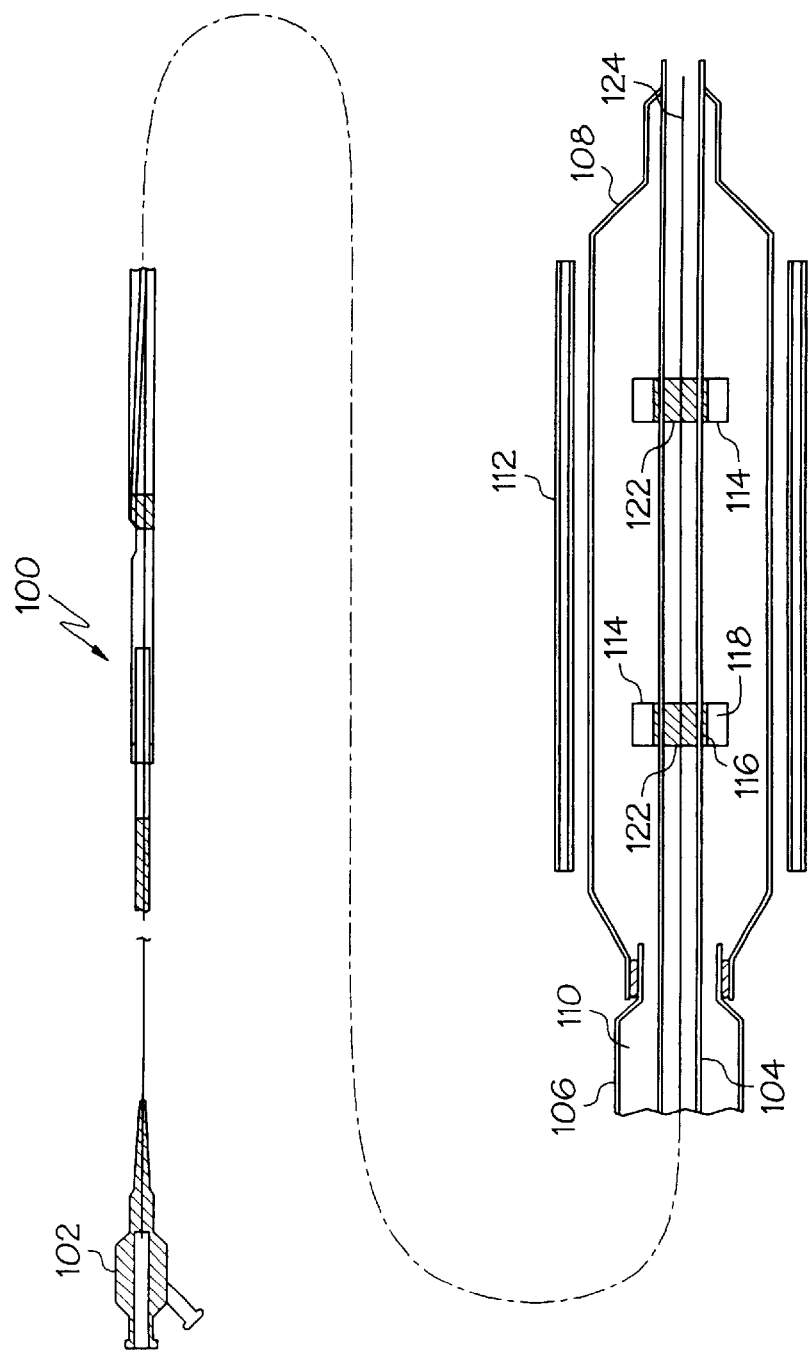

STENT DELIVERY SYSTEM WITH IMPROVED TRACKING

BACKGROUND OF THE INVENTION

Stents are tubular devices designed to maintain the patency of a bodily vessel. Stents have been used in a number of different parts of the body including the vasculature, the urinary system, the biliary ducts and the esophagus. A stent is typically delivered to a desired bodily location via a stent delivery system such as a catheter. The stent, disposed about the distal end of the catheter, is inserted in a bodily vessel and delivered to the desired bodily location where it is then deployed.

Stents may be self-expanding, mechanically expandable or hybrids. Examples of self-expanding stents include coil stents and stents made from shape memory materials such as nitinol. One such stent is disclosed in copending, commonly assigned U.S. application Ser. No. 08/511076. Mechanically expandable stents are most often expanded by medical balloons. Such stents are typically made of metals such as stainless steel. An example of the latter is disclosed in U.S. Pat. No. 6,033,433. Hybrid stents may be mechanically expandable in part and self-expanding in part. An example of such a stent is disclosed in copending, commonly assigned U.S. application Ser. No. 09/087526.

In delivering stents, it is important to prevent slippage of the stent on the catheter. A number of techniques to prevent slippage have been disclosed. Copending, commonly assigned U.S. application Ser. No. 09/283375 discloses the use of a balloon with protrusions thereon to grip a stent. The use of securement hubs and other stent securement means disposed about the catheter inner tube is disclosed in U.S. Pat. No. 6,096,056, U.S. Pat. No. 6,007,543, U.S. Pat. No. 5,968,069, U.S. Pat. No. 5,944,726 and U.S. Pat. No. 5,653,691. The use of securement hubs is complicated, however, because when the stent is crimped to the balloon, the force applied to the securement hubs may cause the inner tube to collapse inward. This, turn, may impair the trackability of the catheter.

There remains a need for innovative securement devices for securing stents and similar medical devices.

All US patents and applications all other published documents mentioned anywhere in this application are incorporated herein by reference in their entirety.

The invention in various of its embodiments is summarized below. Additional details of the invention and/or additional embodiments of the invention may be found in the Detailed Description of the Invention below.

BRIEF SUMMARY OF THE INVENTION

In one embodiment, the invention is directed to a medical device delivery system comprising an inner tube having a proximal end and a distal end. At least one securement hub is disposed about the distal end of the inner tube. The securement hub comprises an inner layer of material and an outer layer of material. The inner layer is made of a material more rigid than the outerlayer. A balloon is disposed about the securement hub and distal end of the inner tube. The balloon is supplied with inflation fluid via an inflation lumen in fluid communication with the balloon. The medical device delivery system may be used for delivering stents by disposing a stent about the balloon. Desirably, the medical device delivery system comprises two or more such securement hubs. Also desirably, the inner layer of the securement hub will be made of a metal and the outer layer will be made of a polymeric material.

In another embodiment, the invention is directed to a medical device delivery system comprising an inner tube with a marker band disposed about the distal end of the inner tube and a securement hub disposed about the marker band. A balloon is disposed about the securement hub and distal end of the inner tube and an inflation lumen is in fluid communication with the balloon. Desirably, the marker band is made from a radiopaque metal. The medical device delivery system may comprise one or more marker bands and one or more securement hubs. Each securement hub is disposed about a marker band. The medical device delivery system may be used for delivering stents by disposing a stent about the balloon.

In another embodiment, the invention is directed to a medical device delivery system comprising an inner tube and a securement hub disposed about the distal end of the inner tube. The securement hub includes an outer layer of a polymeric material and an inner layer. The inner layer is more rigid than the inner tube. A balloon is disposed about the securement hub and the distal end of the inner tube and an inflation lumen is in fluid communication with the balloon.

In yet another embodiment, the invention is directed to a medical device delivery system comprising an inner tube having a proximal end and a distal end and a multilayer securement hub disposed about the distal end of the inner tube. The multilayer securement hub is composed of a plurality of layers of material including a first layer of a first material and a second layer of a second material. The second material differs from the first material. A balloon is disposed about the multilayer securement hub and distal end of the inner tube and an inflation lumen is in fluid communication with the balloon.

A detailed description of the invention in its various embodiments is provided below.

BRIEF DESCRIPTION OF THE SEVERAL VIEWS OF THE DRAWING(S)

FIG. 3 is an isometric view, a portion of which is enlarged and in longitudinal section of an inventive medical device delivery system;

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

In the description that follows, the term "stent" is intended to refer to stents, stent-grafts and grafts.

Figure 1:
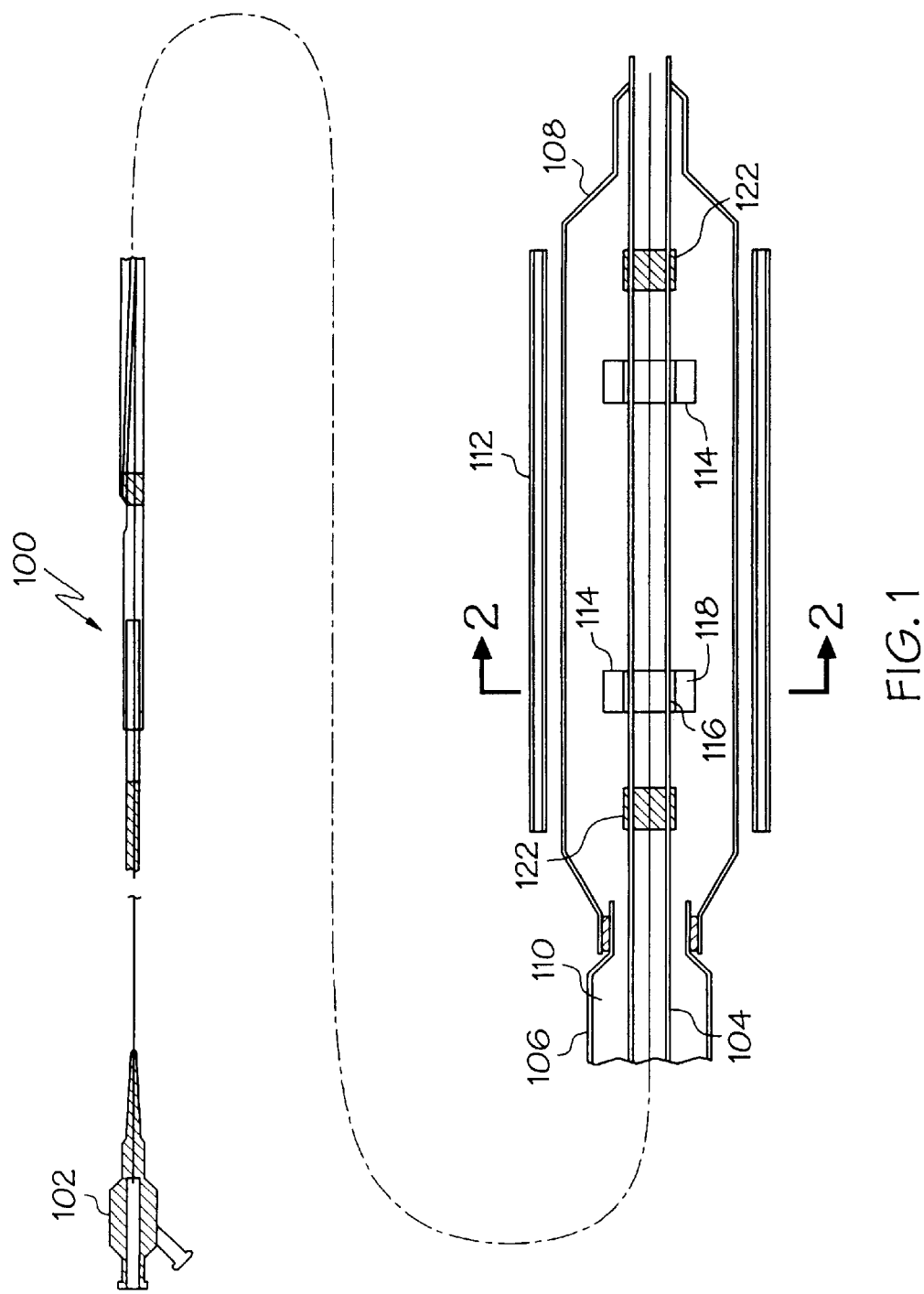
FIG. 1 is an isometric view, a portion of which is enlarged and in longitudinal section of an inventive medical device delivery system.

A medical device delivery system is shown generally at 100 in FIG. 1. Medical device delivery system 100 includes a manifold 102 at the proximal end, an inner tube 104 extending in the distal end of the system and an outer tube 106. Balloon 108 is affixed at the proximal end to the distal end of outer tube. Balloon 108 is disposed about the distal end of inner tube 104. The distal end of balloon 108 is affixed to inner tube 104. Balloon 108, shown in a partially inflated state, is affixed to the inner and outer tubes via standard means such as adhesives or heat bonding (for example, laser welding). Balloon 108 is supplied with an inflation fluid via inflation lumen 110 which extends to the proximal end of the system. As shown in FIG. 1, the distal end of the inflation lumen 110 consists of the space between outer tube 106 and inner tube 104. The inflation lumen may also be provided in the form of a separate shaft extending from the distal end of the medical device delivery system to balloon 108 or in any other suitable form. The illustrated system is a rapid exchange system. Guidewire 124 enters inner tube 104 via guidewire port 126 which is disposed between the manifold and the distal end of the delivery system. However, other types of systems may be used such as over-the-wire and fixed wire systems. An example of an over-the-wire system is disclosed in U.S. Pat. No. 5,980,533. An example of a fixed-wire catheter is disclosed in U.S. Pat. No. 5,702,364. Medical device delivery system 100 may further comprise a retractable sheath (not shown) disposed about stent 112 and an associated retraction device. Medical device delivery system 100 may further comprise one or more retention sleeves as discussed below.

Medical device delivery system 100 optionally includes at least one marker band 122 and desirably a plurality of marker bands. The marker band may be bonded adhesively to the inner tube, swaged to the inner tube or secured to the inner tube via any other suitable method. Marker band 122 may comprise one or more rings, one or more spirals, combinations thereof or may be of any other known marker band design.

The medical device delivery system of FIG. 1 also includes a stent 112 disposed about balloon 108 and is configured for use as a stent delivery system. Stent 112 may be any suitable balloon expandable stent as known in the art.

Figure 2:
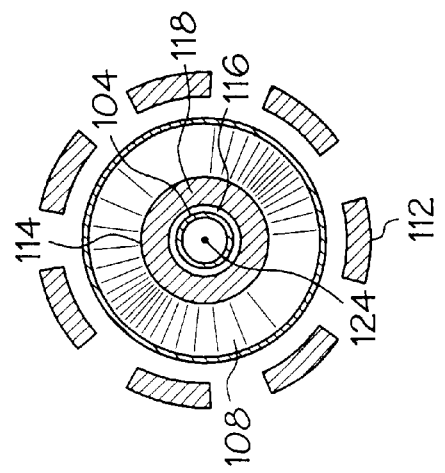
FIG. 2 is a transverse cross-sectional view taken along line 2—2 of FIG. 1.

Securement hubs 114 extend from inner tube 104 interior to balloon 108. Securement hubs 114, shown in greater detail in FIG. 2, are generally tubular. Securement hubs 114 comprise an inner layer 116 and an outer layer 118. Inner layer 116 is made of a material more rigid than outer layer 118. Desirably, inner layer 116 is made of a metal such as stainless steel, gold and gold alloys, platinum and platinum alloys, silver and silver alloys or other metals. Where the metal is radiopaque, such as for example, gold, the inner layer may serve as a marker band. To that end, the invention contemplates a marker band forming an inner layer of a securement hub, as shown in FIG. 3, where the marker band is made of a material more rigid than the securement hub.

Desirably, outer layer 118 is made of a polymeric material and more desirably of a resilient polymeric material. The deformation of resilient material of the securement hub when a stent/balloon is crimped to it causes a radial outward force on the stent/balloon increasing the friction therebetween despite a recoil of the stent. Suitable polymeric materials include any deformable thermoplastic material, desirably an elastomer material and more desirably a relatively resilient elastomer material, e.g., lower durometer silicone. For example, low density polyethylene (LDPE), a lower durometer silicone or a urethane may be used.

In the embodiment of FIGS. 1–3, two securement hubs are present. The invention also contemplates the use of a single securement hub as well as the use of a plurality of securement hubs. To that end, three, four, five, six or more securement hubs may be provided.

Figure 5:
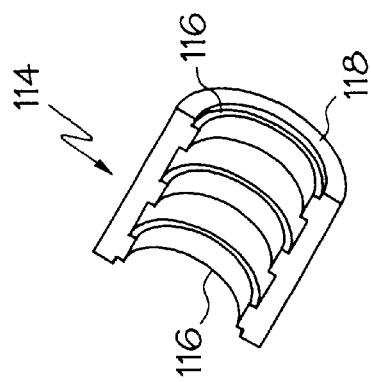
FIG. 5 is perspective view of an inventive securement hub with parts cut away.
Figure 4:
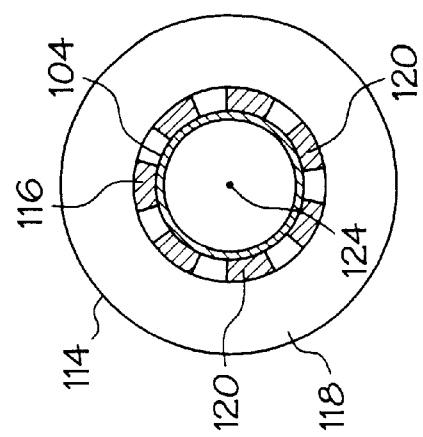
FIG. 4 is a transverse cross-sectional view of an inventive securement hub disposed about an inner tube.

Inner layer 116 may be continuous and of generally tubular shape as shown in FIG. 2. The invention also contemplates a securement having a more rigid inner layer 116 which is not continuous. As shown in FIG. 4, inner layer 116 consists of a plurality of discontinuous strips 120 (shown shaded). The inner layer may also be provided in the form of a plurality of spaced rings 116, as shown in FIG. 5, a spiral of material or a grid of material.

Securement hubs 114 may be secured to inner tube 104 via any suitable bonding technique. Where the inner layer of the securement hub is made of a polymeric material, the securement hub may be heat bonded to the inner tube. Other techniques for affixing the securement hubs to the inner tube include the use of adhesives as are known in the art and swaging the securement hub to the inner tube. The securement hubs may also be secured to the inner tube via a friction fit. The invention also contemplates the use of securement hubs which are movable, for example, slidable in an axial direction.

In another embodiment, the invention is directed to a medical device delivery system comprising an inner tube and a securement hub disposed about the distal end of the inner tube. The securement hub includes an outer layer of a polymeric material and an inner layer. The inner layer is more rigid than the inner tube in the region of the securement hub. The securement hub may be in the form of a ring or may incorporate any of the other physical designs disclosed above. The proximal end of the balloon may extend from the distal end of an outer tube and the distal end of the balloon may be attached to the inner tube as shown in FIG. 1. The medical device delivery system may further comprise a stent disposed about the inner tube, balloon and securement hub.

In yet another embodiment, the invention is directed to a medical device delivery system comprising an inner tube and a securement hub disposed about the distal end of the inner tube. The securement hub includes an outer layer of a polymeric material and an inner layer. The inner layer is made of a different material having a different composition from the outer layer. One of the layers may be made of a metal and the other layer may be made from a polymeric material. Alternatively, one of the layers may be made of a first polymeric material and the other layer may be formed of a second, different polymeric material. The polymeric materials may differ from one another in chemical properties and/or in physical properties. For example, the outer layer may be made of LDPE and the inner layer may be made of high density polyethylene (HDPE) or a high durometer urethane. Other suitable materials include PET, nylon and polypropylene. The securement hub may be in the form of a ring or may incorporate any of the other physical designs disclosed above.

The medical device delivery system may further comprise a balloon disposed about the inner tube. The proximal end of the balloon may extend from the distal end of an outer tube and the distal end of the balloon may be attached to the inner tube as shown in FIG. 1. Any other balloon arrangement may also be used. The medical device delivery system may further comprise a stent disposed about the inner tube, balloon and securement hub. A retractable sheath may be provided to protect the stent prior to deployment. Retention sleeves, sometimes referred to as socks, may also be provided, as discussed below.

The securement hubs disclosed herein may assume shapes other than the generally tubular shape shown in the figures. The securement hubs may be spiral or otherwise wound about the inner tube or may be cylindrical with cuts therein or other patterns. The entirety of the hub may be spiral or of another shape or one of the layers may be spiral or of another shape. The entirety of the outer surface of the securement hubs may extend a substantially constant distance radially from the inner tube or different portions of the outer surface of the securement hubs may extend different distances from the inner tube. As examples of the latter, the securement hubs may be accordion shaped or corrugated. Other suitable shapes are disclosed in U.S. Pat. No. 5,968,069

The securement hubs disclosed herein may be of a two layer construction or may comprise additional layers. For example, the invention contemplates securement hubs having three or more layers where at least two of the layers have different compositions. The invention also contemplates securement hubs having three or more layers including an inner layer of greater rigidity than an outer layer.

Securement hubs in accordance with the invention may extend under a portion of the stent as shown in FIG. 1 or under the entirety of the stent. The invention further contemplates the use of a securement hub whose length exceeds that of the stent.

The inventive medical device delivery systems disclosed herein may be provided with inventive securement hubs as disclosed herein which are fixed in place on the inner tube or which are movable relative to the inner tube. Additional details concerning movable securement hubs may be found in U.S. Pat. No. 5,968,069.

In addition to the securement hubs, the inventive medical device delivery systems may comprise at least one sleeve disposed about the end of the medical device or stent to aid in retaining the medical device on the inner tube. Desirably, the sleeve will be adhesively bonded or welded to the inner tube or balloon. The invention also contemplates the use of one or more sleeves which frictionally engage the inner tube. The sleeves may be continuous in the region where they overlap the medical device or stent or they may be non-continuous. For example, the sleeves may be in the form of a coil. The sleeves may be made of a radiopaque material or may include radiopaque materials in their construction so as to exhibit radiopacity over at least a portion of the sleeve. At least one of the sleeves, desirably, the proximal sleeve, may optionally comprise a retraction mechanism to retract the sleeve from the medical device. Additional details concerning the construction of sleeves may be found in copending, commonly assigned U.S. application Ser. Nos. 09/407836 and 09/427805.

The inventive medical device delivery systems may be provided configured for rapid exchange, for use as an over-the wire system or as a fixed wire system.

In addition to the specific embodiments claimed below, the invention is also directed to other embodiments having any other possible combination of the dependent features described above and/or claimed below.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A medical device delivery system comprising:
   an inner tube having a proximal end and a distal end;
   at least one securement hub disposed about the distal end of the inner tube, the securement hub comprising an inner layer of material and an outer layer of material, the inner layer of material more rigid than the outer layer of material, wherein the outer layer is in contact with the inner layer and the outer layer is not in contact with the inner tube;
   a balloon disposed about the securement hub and the distal end of the inner tube;
   an inflation lumen in fluid communication with the balloon; and
   a stent disposed about the balloon and the at least one securement hub, the stent having a length starting at a first end of the stent and terminating at a second end of the stent, wherein the at least one securement hub is positioned between the first and second ends of the stent.

2. The medical device delivery system of claim 1 wherein the outer layer of the at least one securement hub is made of a polymeric material.

3. The medical device delivery system of claim 1 comprising two or more axially spaced securement hubs disposed about the inner tube, each securement hub comprising an inner layer of material and an outer layer of polymeric material, the inner layer of material more rigid than the outer layer of material, the balloon disposed about both securement hubs, wherein the securement hubs are positioned between the first and second ends of the stent.

4. The medical device delivery system of claim 1 wherein the inner layer of the at least one securement hub is formed of metal.

5. The medical device delivery system of claim 4 wherein the outer layer of the at least one securement hub is formed of a polymeric material selected from the group consisting of polyurethane and low density polyethylene.

6. The medical device delivery system of claim 1 wherein the inner layer of the at least one securement hub is selected from the group consisting of one or more rings and one or more spirals.

7. The medical device delivery system of claim 6 wherein the inner layer of the at least one securement hub is in the form of a metal ring.

8. The medical device delivery system of claim 1 wherein the securement hub is adhesively secured to the inner tube or heat bonded to the inner tube of the at least one securement hub.

9. The medical device delivery system of claim 1 wherein the inner layer of the at least one securement hub comprises a plurality of discontinuous strips.

10. A medical device delivery system comprising:
    an inner tube having a proximal end and a distal end;
    a marker band disposed about the distal end of the inner tube;
    a securement hub disposed about the marker band, wherein the securement hub is in contact with the marker band and the securement hub is not in contact with the inner tube;
    a balloon disposed about the securement hub and distal end of the inner tube;
    a stent disposed about the balloon and securement hub, the stent having a length starting at a first end of the stent and terminating at a second end of the stent, wherein the securement hub is positioned between the first and second ends of the stent; and an inflation lumen in fluid communication with the balloon.

11. The medical device delivery system of claim 10 wherein the marker band is formed of a radiopaque metal.

12. The medical device delivery system of claim 10 wherein the marker band is more rigid than the hub.

13. The medical device delivery system of claim 10 comprising a plurality of securement hubs, and a plurality of marker bands, each securement hub disposed about a marker band, wherein the securement hubs are positioned between the first and second.

14. The medical device delivery system of claim 10 wherein the securement hub is made of a polymeric material.

15. The medical device delivery system of claim 10 wherein the securement hub is adhesively secured to the marker band.

16. The medical device delivery system of claim 10 wherein the marker band is adhesively bonded or swaged to the inner tube.

17. The medical device delivery system of claim 10 wherein the marker band is selected from the group consisting of at least one ring and at least one spiral and combinations thereof.

18. A medical device delivery system comprising:

an inner tube having a proximal end and a distal end;

a securement hub disposed about the distal end of the inner tube, the securement hub including an outer layer of a polymeric material and an inner layer, the inner layer more rigid than the inner tube, wherein the outer layer is in contact with the inner layer and the outer layer is not in contact with the inner tube;

a balloon disposed about the securement hub and distal end of the inner tube;

a stent disposed about the balloon and securement hub, the stent having a length starting at a first end of the stent and terminating at a second end of the stent, wherein the securement hub is positioned between the first and second ends of the stent; and an inflation lumen in fluid communication with the balloon.

19. A medical device delivery system comprising:

an inner tube having a proximal end and a distal end;

a multilayer securement hub disposed about the distal end of the inner tube, the multilayer securement hub composed of a plurality of layers of material including a first layer of a first material and a second layer of a second material, the second material having a composition different from the composition of the first material, wherein the first layer is in contact with the second layer and the first layer is not in contact with the inner tube;

a balloon disposed about the securement hub and distal end of the inner tube;

a stent disposed about the balloon and securement hub, the stent having a length starting at a first end of the stent and terminating at a second end of the stent, wherein the multilayer securement hub is Positioned between the first and second ends of the stent; and an inflation lumen in fluid communication with the balloon.

20. The medical device delivery system of claim 19 wherein the second material is more rigid than the first material.

21. The medical device delivery system of claim 20 wherein the second material is disposed between the first material and the inner tube.

22. The medical device delivery system of claim 18 further comprising a retaining sleeve disposed over an end of the stent and over a portion of the inner tube.

23. The medical device delivery system of claim 22 wherein at least a portion of the retaining sleeve is radiopaque.

24. The medical device delivery system of claim 17, having two multilayer securement hubs positioned between the first and second ends of the stent.

* * * * *